United States Patent [19]
Sakaguchi et al.

[11] Patent Number: 5,723,664
[45] Date of Patent: Mar. 3, 1998

[54] METHOD OF PREPARING SULFONIMIDE OR ITS SALT

[75] Inventors: Hiroaki Sakaguchi; Kenji Fujii; Shigenori Sakai; Yoshiyuki Kobayashi; Yasushi Kita, all of Ube, Japan

[73] Assignee: Central Glass Company, Limited, Yamaguchi, Japan

[21] Appl. No.: 525,439

[22] Filed: Sep. 7, 1995

[30] Foreign Application Priority Data

Sep. 12, 1994 [JP] Japan ................... 6-217532

[51] Int. Cl.$^6$ ......................................... C07C 303/38
[52] U.S. Cl. ......................................... 564/82
[58] Field of Search ......................................... 564/82

[56] References Cited

U.S. PATENT DOCUMENTS

| | | | |
|---|---|---|---|
| 2,292,997 | 8/1942 | Hentrich et al. | 260/556 |
| 2,341,614 | 2/1944 | Hentrich et al. | 564/82 |
| 5,256,821 | 10/1993 | Armand | 564/82 |
| 5,502,251 | 3/1996 | Pohmer | 564/82 |

FOREIGN PATENT DOCUMENTS

| | | | |
|---|---|---|---|
| 0571832 | 12/1993 | European Pat. Off. | 564/82 |
| 3-501860 | 4/1991 | Japan . | |

OTHER PUBLICATIONS

Chemiker–Zeitung, vol. 96, No. 10, 1972, pp. 582–583, XP002019684 J.N. Muessdoerffer et al.
Foropoulos et al. (1984) "Inorganic Chemistry", vol. 23, No. 23, pp. 3720–3723.

*Primary Examiner*—Peter O'Sullivan
*Attorney, Agent, or Firm*—Keck, Mahin & Cate

[57] ABSTRACT

The invention relates to a method of preparing a sulfonimide, a first salt thereof, or a second salt thereof. The method includes the step of: (a) reacting one or two sulfonyl fluorides with nonhydrous ammonia and an amine component which is one of a tertiary amine and a heterocyclic amine, so as to prepare the first salt. Alternatively, the method includes the step of: (a) reacting the sulfonyl fluoride with the amine component and a sulfonamide, so as to prepare the first salt. The method further optionally includes, after the step (a), the step of: (b) reacting, in an aqueous solution, the first salt with a metal compound, so as to prepare the second salt. The method still further optionally includes, after the step (a), the step of: (c) reacting the first salt with a strong acid so as to prepare the sulfonimide. Alternatively, the method further optionally includes, after the step (b), the step of: (d) reacting the second salt with a strong acid so as to prepare the sulfonimide. The sulfonimide, the first salt or the second salt is easily economically prepared in an industrial scale production with high purity and high yield.

14 Claims, No Drawings

METHOD OF PREPARING SULFONIMIDE OR ITS SALT

BACKGROUND OF THE INVENTION

The present invention relates to a method of preparing a sulfonimide or its salt. Sulfonimide compounds are useful as Lewis acid catalysts and ion transport agents, in the fields of organic compound syntheses, electrolytes and the like.

Foropoulos et al. (1984) Inorganic Chemistry, vol. 23, No. 23, pp. 3720–3723 discloses a method of synthesizing a sulfonimide represented by the formula of $(CF_3SO_2)_2NH$. This method may not be appropriate in an industrial scale production, because it is necessary to have many reaction steps and to use an expensive substance, hexamethyldisilazane, and because the yield is as low as about 50%.

Japanese Patent Publication No. "Kohyo" 3-501860 discloses another method of synthesizing a sulfonimide. In this method, a silazane component is reacted with at least one halogenated sulfonyl component. This method is not an economical one, because an expensive substance, the silazane component, is used as the nitrogen source of the sulfonimide.

SUMMARY OF THE INVENTION

It is therefore an object of the present invention to provide a method of preparing a sulfonimide or its salt, which method is economical in an industrial scale production.

According to the present invention, there is provided a first method of preparing a sulfonimide represented by the general formula (1), a first salt thereof represented by the general formula (2), or a second salt thereof represented by the general formula (3), the method comprising the step of:

(a) reacting one or two sulfonyl fluorides represented by the general formula (4) with nonhydrous ammonia and an amine component which is one of a tertiary amine represented by the general formula (5) and a heterocyclic amine, so as to prepare said first salt, $$H[Rf^1SO_2-N-SO_2Rf^2] \quad (1)$$

wherein "$Rf^1$" and "$Rf^2$" represent the same or different groups each of which has a carbon atom number from 1 to 12 and is straight-chain or branched-chain and one selected from the group consisting of perfluoroalkyl groups, fluoroalkyl groups, fluoroalkenyl groups and fluoroallyl groups, $$M^1[Rf^1SO_2-N-SO_2Rf^2]_{n1} \quad (2)$$

wherein "$Rf^1$" and "$Rf^2$" are defined as above; "$M^1$" represents a positive ion having a first valence; and "n1" represents an integer that is the same as said first valence, $$M^2[Rf^1SO_2-N-SO_2Rf^2]_{n2} \quad (3)$$

wherein "$Rf^1$" and "$Rf^2$" are defined as above; "$M^2$" represents an alkali or alkali earth metal atom having a second valence; and "n2" represents an integer that is the same as said second valence, $$RfSO_2F \quad (4)$$

wherein "Rf" represents the same or different groups which are identical with said "$Rf^1$" and said "$Rf^2$", $$(R^1)_3N \quad (5)$$

wherein "$R^1$" represents the same or different alkyl groups each having a carbon atom number from 1 to 5.

According to the present invention, there is provided a second method of preparing the sulfonimide, the first salt thereof, or the second salt thereof, the method comprising the step of:

(a) reacting the sulfonyl fluoride with the amine component and a sulfonamide represented by the general formula (6), $$RfSO_2NH_2 \quad (6)$$

wherein "Rf" is defined as above.

In the invention, the above-mentioned first or second method further optionally comprises, after the step (a), the step of: (b) reacting, in an aqueous solution, the first salt with a metal compound selected from the group consisting of hydroxides, oxides and carbonates, the metal compound containing the alkali or alkali earth metal atom, so as to prepare the second salt.

In the invention, the first or second method still further optionally comprises, after the step (a), the step of: (c) reacting the first salt with a strong acid so as to prepare the sulfonimide.

In the invention, the first or second method still further optionally comprises, after the step (b), the step of: (d) reacting the second salt with a strong acid so as to prepare the sulfonimide.

The sulfonimide, the first salt thereof or the second salt thereof can be easily economically produced in an industrial scale production with high purity and high yield, by the first or second method of the present invention. The inventors have unexpectedly found such method that is free from the above-mentioned drawbacks, by using the above-mentioned amine component.

DESCRIPTION OF THE PREFERRED EMBODIMENTS

According to the present invention, there are provided first and second methods of preparing a sulfonimide represented by the general formula (1) (hereinafter referred to as "the sulfonimide (1)"), a first salt thereof represented by the general formula (2) (hereinafter referred to as "the first salt (2)"), or a second salt thereof represented by the general formula (3) (hereinafter referred to as "the second salt (3)").

$$H[Rf^1SO_2-N-SO_2Rf^2] \quad (1)$$

wherein "$Rf^1$" and "$Rf^2$" represent the same or different groups each of which has a carbon atom number from 1 to 12 and is straight-chain or branched-chain and one selected from the group consisting of perfluoroalkyl groups, fluoroalkyl groups, fluoroalkenyl groups and fluoroallyl groups, $$M^1[Rf^1SO_2-N-SO_2Rf^2]_{n1} \quad (2)$$

wherein "$Rf^1$" and "$Rf^2$" are defined as above; "$M^1$" represents a positive ion having a first valence; and "n1" represents an integer which is the same as said first valence, $$M^2[Rf^1SO_2-N-SO_2Rf^2]_{n2} \quad (3)$$

wherein "$Rf^1$" and "$Rf^2$" are defined as above; "$M^2$" represents an alkali or alkali earth metal atom having a second valence; and "n2" represents an integer which is the same as said second valence.

The first method of preparing the sulfonimide (1), the first salt thereof (2), or the second salt thereof (3) comprises the step of:

(a) reacting one or two sulfonyl fluorides represented by the general formula (4) (hereinafter referred to as "the sulfonyl fluoride (4)") with nonhydrous ammonia and an amine component which is one of a tertiary amine represented by the general formula (5) (hereinafter referred to as "the tertiary amine (5)") and a heterocyclic amine, so as to prepare the first salt (1), $$RfSO_2F \tag{4}$$

wherein "Rf" represents the same or different groups which are identical with said "$Rf^1$" and said "$Rf^2$".

$$(R^1)_3N \tag{5}$$

wherein "$R^1$" represents the same or different alkyl groups each having a carbon atom number from 1 to 5.

The first salt (2) is a combination of the sulfonimide (1) and the amine component which is one of the tertiary amine (5) and a heterocyclic amine. Examples of the tertiary amine (5) are trimethylamine, triethylamine and tributylamine. Examples of this heterocyclic amine are pyridine and picoline. These examples of the amine component are preferable ones because it is possible to easily distill these ones out from the reaction system at a relatively low temperature. The second salt (3) is an alkali or alkali metal salt of the sulfonimide (1).

In the first method, it is possible to prepare the sulfonimide (1) having "$Rf^1$" and "$Rf^2$" which are the same groups, by reacting, in an inert solvent, one sulfonyl fluoride (4) with nonhydrous ammonia and the amine component, and it is possible to prepare the sulfonimide (1) having "$Rf^1$" and "$Rf^2$" which are different groups, by reacting, in an inert solvent, two equimolar sulfonyl fluorides (4) with nonhydrous ammonia and the amine component.

In order to obtain a higher yield, it is preferable to react about 1 part by mol of one sulfonyl fluoride (4) with about 1 part by mol of nonhydrous ammonia and about 1 part by mol of the amine component in case that "$Rf^1$" and "$Rf^2$" of the sulfonimide (1) are the same groups, and it is preferable to react about 2 part by mol of the total of the two equimolar sulfonyl fluorides (4) with about 2 part by mol of nonhydrous ammonia and about 2 parts by mol of the amine component in case that "$Rf^1$" and "$Rf^2$" of the sulfonimide (1) are different groups. In either case that "$Rf^1$" and "$Rf^2$" of the sulfonimide (1) are the same groups or different groups, when an excessive amount of anhydrous ammonia is added, a large amount of sulfonamide is produced, thereby lowering yield of the sulfonimide (1). In contrast, the amine component may be excessively added. If desired, the amine component may be used as a solvent.

The reaction in the step (a) of the first method is expressed as the following reaction formula (1) in case that the tertiary amine (5) is used as the amine component and that "$Rf^1$" and "$Rf^2$" of the sulfonimide (1) are the same groups (Rf).

$$2RfSO_2F+2NH_3+2(R^1)_3N \rightarrow (R^1)_3NH^+(RfSO_2)_2N^- +(R^1)_3NH^+F^- + NH_4F \tag{1}$$

The reaction in the step (a) of the first method is expressed as the following reaction formula (2) in case that the tertiary amine (5) is used as the amine component and that "$Rf^1$" and "$Rf^2$" of the sulfonimide (1) are different groups.

$$Rf^1SO_2F+Rf^2SO_2F+2NH_3+2(R^1)_3N \rightarrow (R^1)_3NH^+(Rf^1SO_2NSO_2Rf^2)^- +(R^1)_3NH^+F^- + NH_4F \tag{2}$$

In the reaction formulas (1) and (2), $(R^1)_3NH^+(RfSO_2)_2N^-$ and $(R^1)_3NH^+(Rf^1SO_2NSO_2Rf^2)^-$ are the reaction products (i.e. the first salt (2)), and $(R^1)_3NH^+F^-$ and $NH_4F$ are by-products.

The step (a) of the first method is conducted preferably at a temperature within a range from about −20° C. to about 200° C. and more preferably at a temperature within a range from about 10° C. to about 80° C. If it is lower than about −20° C., the reaction rate becomes substantially slow. If it is higher than about 200° C., the raw materials of the reaction and the reaction product may be decomposed.

In the step (a) of the first method, it is possible to use a solvent not limited to a particular type, as long as it is inert in the reaction. Examples of this solvent are halogenated hydrocarbons such as dichloromethane, ethylene chloride and perfluorocarbons; hydrocarbons such as benzene, heptane and cyclohexane; acetal such as dioxane; ethers such as diethyl ether and diisopropyl ether; and nitriles such as acetonitrile.

For example, when dichloromethane is used as a solvent in the first method, $NH_4F$ as a by-product is insoluble therein. Therefore, $NH_4F$ can be easily removed by filtration. Then, the solvent in the filtrate can be distilled out. With this, a first mixture of the sulfonimide-substituted ammonium salt (i.e. the first salt (1)) and the amine salt of hydrofluoric acid can be obtained.

The first method of preparing the sulfonimide (1), the first salt thereof (2), or the second salt thereof (3) further comprises the step of:

(b) reacting, in an aqueous solution, the first salt (1) or the first mixture containing the first salt (1) with a metal compound which is selected from the group consisting of hydroxides, oxides and carbonates and contains the alkali or alkali earth metal atom corresponding to "$M^{2+}$" of the second salt (2), so as to prepare the second salt (2).

The reaction in the step (b) of the first method is expressed as the following reaction formulas (3) and (4) in case that LiOH and Ca(OH)$_2$ are respectively used as the metal compound.

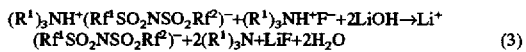

$$(R^1)_3NH^+(Rf^1SO_2NSO_2Rf^2)^- + (R^1)_3NH^+F^- + 2LiOH \rightarrow Li^+(Rf^1SO_2NSO_2Rf^2)^- + 2(R^1)_3N + LiF + 2H_2O \tag{3}$$

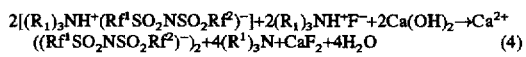

$$2[(R_1)_3NH^+(Rf^1SO_2NSO_2Rf^2)^-] + 2(R_1)_3NH^+F^- + 2Ca(OH)_2 \rightarrow Ca^{2+}((Rf^1SO_2NSO_2Rf^2)^-)_2 + 4(R^1)_3N + CaF_2 + 4H_2O \tag{4}$$

In the step (b), the cations (i.e. $(R^1)_3NH^+$) of the first mixture are replaced by the cations of the metal compound (i.e. the alkali metal or alkali earth metal ions), thereby releasing the tertiary amine (5). Then, a second mixture of the second salt (3) and a metal fluoride can be obtained by distilling out the tertiary amine (5) and water. Then, an ether, an alcohol or the like is added to the second mixture. Then, the metal fluoride is filtered out. Then, the solvent is distilled out from the filtrate, to thereby obtain the second salt (3) with high purity. Alternatively, in case that the metal fluoride has a small solubility in water, the following two steps suffices for obtaining the second salt (3) with high purity. That is, after the step (b), the metal fluoride is filtered out. Then, water and the tertiary amine (5) are distilled out, thereby obtaining the second salt (3) with high purity.

The second method of preparing the sulfonimide (1), the first salt thereof (2), or the second salt thereof (3) is described in the following. The second method comprises the step of:

(a) reacting the sulfonyl fluoride (4) with a sulfonamide represented by the general formula (6) (hereinafter referred to as "the sulfonamide (6)") and the amine component which is one of the tertiary amine (5) and a heterocyclic amine, so as to prepare the first salt, $$Rf^2SO_2NH_2 \tag{6}$$

wherein "Rf²" is defined as above.

The reaction of the step (a) of the second method can be also conducted in an inert solvent. The sulfonamide (6) can be synthesized by a known method disclosed in, for example, Foropoulos et al. (1984) Inorganic Chemistry, vol. 23, No. 23, pp. 3720–3723.

"Rf" in the sulfonyl fluoride (4) and "Rf" in the sulfonamide (6) are either the same or different groups. In order to obtain high yield, it is preferable that about 1 part by mol of the sulfonyl fluoride (4) is reacted with about 1 part by mol of the sulfonamide (6) and about 2 parts by mol of the amine component.

The reaction in the step (a) of the second method is expressed as the following reaction formula (5) in case that the tertiary amine (5) is used as the amine component.

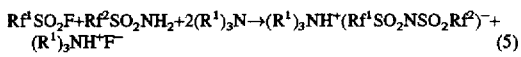

$$Rf^1SO_2F + Rf^2SO_2NH_2 + 2(R^1)_3N \rightarrow (R^1)_3NH^+(Rf^1SO_2NSO_2Rf^2)^- + (R^1)_3NH^+F^- \quad (5)$$

In the second method, the reaction temperature of the step (a) has the same preferable and more-preferable ranges as those in the first method. The solvent for the step (a) of the second method is not limited to a particular type as long as it is inert in the reaction. It is possible to use the same examples of the solvent as in the first method.

Similar to the first method, the solvent is distilled out after the reaction of the step (a), thereby obtaining the first mixture of the sulfonimide-substituted ammonium salt (i.e. the first salt (1)) and the amine salt of hydrofluoric acid. Then, the first mixture is reacted in an aqueous solution with the same metal compound as in the first method, thereby obtaining the second salt (3) with high purity.

It is possible to synthesize the sulfonimide (1) by reacting the first or second salt (2 or 3) prepared by the first or second method, with a strong acid such as concentrated sulfuric acid, followed by distillation. If the thus synthesized sulfonimide (1) is reacted with metal hydroxides, metal oxides, metal carbonates, metal acetates, ammonia or substituted ammonias, the various corresponding sulfonimide salts are produced.

The following examples are illustrative of the present invention, but these examples are not limitative. In each of Examples 1–10, the first salt was identified by NMR spectroscopy.

EXAMPLE 1

In this example, the second salt (3) of the sulfonimide (1) was prepared by the steps (a) and (b) of the first method according to the present invention as follows.

The step (a) was conducted for obtaining the first salt (1) as follows. At first, an autoclave made of stainless steel was charged with 40 ml of dichloromethane and 13.5 g of triethylamine. The reaction vessel was cooled down to –40° C. Then, 2.3 g of anhydrous ammonia and 20.0 g of trifluoromethanesulfonyl fluoride ($CF_3SO_2F$) were introduced thereinto. Then, the temperature of the reaction vessel was increased to 20° C. and the reaction solution was stirred for 3 hr. Ammonium fluoride as a by-product was filtered out from the reaction mixture. Then, the solvent was distilled out from the filtrate, thereby obtaining a first mixture of the first salt, i.e. triethylammonium salt of bis((trifluoromethyl)sulfonyl) imide [$(C_2H_5)_3NH^+(CF_3SO_2)_2N^-$], and triethylammonium fluoride [$(C_2H_5)_3NH^+F^-$].

Then, the step (b) was conducted as follows. The thus prepared first mixture was mixed with an aqueous solution containing 3.2 g of lithium hydroxide. After the reaction, the insoluble lithium fluoride was filtered out from the reaction mixture. Then, triethylamine and water as by-products were distilled out from the filtrate, to thereby obtain the second salt, i.e. lithium salt of bis((trifluoromethyl)sulfonyl) imide [$Li(CF_3SO_2)_2N$]. Then, ether was added to this second salt, followed by the removal of the insoluble. Then, this ether was distilled out, to thereby obtain 17.8 g of the second salt having a purity of at least 99%. The yield was 94%.

EXAMPLE 2

In this example, the second salt (3) of the sulfonimide (1) was prepared by the first method. In fact, Example 1 was repeated except in that the step (b) was modified as follows. The first mixture prepared in accordance with the step (a) of Example 1 was mixed with an aqueous solution containing 5.3 g of sodium hydroxide. After the reaction, the insoluble sodium fluoride was filtered out from the reaction mixture. Then, triethylamine and water as by-products were distilled out from the filtrate, thereby obtaining the second salt, i.e. sodium salt of bis((trifluoromethyl)sulfonyl) imide [$Na(CF_3SO_2)_2N$]. Then, ether was added to this second salt, followed by the removal of the insoluble. Then, this ether was distilled out, so as to obtain 19.1 g of the second salt having a purity of at least 99%. The yield was 96%.

EXAMPLE 3

In this example, the second salt (3) of the sulfonimide (1) was prepared by the first method. In fact, Example 2 was repeated except in that the step (a) for obtaining the first salt was modified as follows.

At first, an autoclave made of stainless steel was charged with 70 ml of dichloromethane, 40.0 g of perfluorobutylsulfonyl fluoride ($C_4F_9SO_2F$) and 11.0 g of pyridine. The reaction vessel was cooled down to –40° C. Then, 2.3 g of anhydrous ammonia was introduced thereinto. Then, the temperature of the reaction vessel was increased to 30° C. and the reaction solution was stirred for 4 hr. Ammonium fluoride as a by-product was filtered out from the reaction mixture. Then, the solvent was distilled out from the filtrate, to thereby obtain a first mixture of the first salt, i.e. pyridinium salt of bis((perfluorobutyl)sulfonyl) imide [$C_5H_5NH^+(C_4F_9SO_2)_2N^-$], and pyridinium fluoride [$C_5H_5NH^+F^-$].

The thus prepared first mixture was subjected to the same treatment as that of the step (b) of Example 2 for obtaining the second salt. With this, 36.2 g of the second salt, i.e. sodium salt of bis((perfluorobutyl)sulfonyl) imide [$Na(C_4F_9SO_2)_2N$] having a purity of at least 99% was obtained. The yield was 91%.

EXAMPLE 4

In this example, the second salt (3) of the sulfonimide (1) was prepared by the steps (a) and (b) of the first method. The step (a) for obtaining the first salt (2) was conducted as follows. At first, an autoclave made of stainless steel was charged with 70 ml of acetonitrile, 40.0 g of perfluorobutylsulfonyl fluoride ($C_4F_9SO_2F$) and 27.3 g of triethylamine. The reaction vessel was cooled down to –40° C. Then, 4.6 g of anhydrous ammonia and 20.0 g of trifluoromethylsulfonyl fluoride ($CF_3SO_2F$) were introduced thereinto. Then, the temperature of the reaction vessel was increased to 40° C. and the reaction solution was stirred for 3 hr. Ammonium fluoride as a by-product was filtered out from the reaction mixture. Then, the solvent was distilled out from the filtrate, to thereby obtain a first mixture of the first salt, i.e. triethylammonium salt of perfluorobutylsulfonyltrifluoromethylsulfonyl imide [$(C_2H_5)_3NH^+$ ($CF_3SO_2NSO_2C_4F_9)^-$], and triethylammonium fluoride [$(C_2H_5)_3NH^+F^-$].

The thus prepared first mixture was subjected to the same treatment as that of the step (b) of Example 2 for obtaining the second salt, except in that the amount of sodium hydroxide was 10.6 g. With this, 53.8 g of the second salt, i.e. sodium salt of perfluorobutylsulfonyltrifluoromethylsulfonyl imide [$Na^+(CF_3SO_2NSO_2C_4F_9)^-$]. The yield was 90%.

EXAMPLE 5

In this example, the second salt (3) of the sulfonimide (1) was prepared by step (a) and (b) of the second method. The step (a) for obtaining the first salt (2) was conducted as follows.

At first, a flask equipped with a condenser using dry ice and ethanol as coolants was charged with 50 ml of dichloromethane. 28.0 g of triethylamine and 20 g of trifluoromethylsulfonyl amide ($CF_3SO_2NH_2$). Then, the reaction vessel was cooled down to $-20°$ C. Then, 21.0 g of trifluoromethylsulfonyl fluoride ($CF_3SO_2F$) was introduced thereinto by spending 2 hr. Then, the temperature of the reaction vessel was increased to $20°$ C. and the reaction solution was stirred for 1 hr. Then, the solvent was distilled out, to thereby obtain a first mixture of the first salt, i.e. triethylammonium salt of bis((trifluoromethyl)sulfonyl) imide [$(C_2H_5)_3NH^+(CF_3SO_2)_2N^-$], and triethylammonium fluoride [$(C_2H_5)_3NH^+F^-$].

The thus prepared first mixture was subjected to the same treatment as that of the step (b) of Example 1 for obtaining the second salt, except in that the amount of lithium hydroxide was 6.6 g. With this, 36.4 g of the second salt, i.e. lithium salt of bis((trifluoromethyl)sulfonyl) imide [$Li^+(CF_3SO_2)_2N^-$] having a purity of at least 99% was obtained. The yield was 95%.

EXAMPLE 6

In this example, Example 5 was repeated except in that the first mixture was mixed with an aqueous solution containing 15 g of potassium hydroxide. With this, 40.6 g of the second salt, i.e. potassium salt of bis((trifluoromethyl) sulfonyl) imide [$K^+(CF_3SO_2)_2N^-$] having a purity of at least 99% was obtained. The yield was 95%.

EXAMPLE 7

In this example, Example 5 was repeated except in that the first mixture was mixed with an aqueous solution containing 20 g of sodium carbonate. With this, 38.2 g of the second salt, i.e. sodium salt of bis((trifluoromethyl)sulfonyl) imide [$Na^+(CF_3SO_2)_2N^-$] having a purity of at least 99% was obtained. The yield was 94%.

EXAMPLE 8

In this example, the second salt (3) of the sulfonimide (1) was prepared by the steps (a) and (b) of the second method. The step (a) for obtaining the first salt (2) was conducted as follows.

At first, a flask was charged with 80 ml of acetonitrile, 42.5 g of perfluorobutylsulfonyl fluoride ($C_4F_9SO_2F$), 23.1 g of pyridine and 20.0 g of trifluoromethylsulfonyl amide ($CF_3SO_2NH_2$). Then, the reaction mixture was stirred at $40°$ C. for 3 hr. Then, the solvent was distilled out, to thereby obtain a first mixture of the first salt, i.e. pyridinium salt of perfluorobutylsulfonyltrifluoromethylsulfonyl imide [$C_5H_5NH^+(CF_3SO_2NSO_2C_4F_9)^-$], and pyridinium fluoride [$C_5H_5NH^+F^-$].

The thus prepared first mixture was subjected to the same treatment as that of the step (b) of Example 1 for obtaining the second salt, except in that the amount of lithium hydroxide was 6.6 g. With this, 53.3 g of the second salt, i.e. lithium salt of perfluorobutylsulfonyltrifluoromethylsulfonyl imide [$Li^+(CF_3SO_2NSO_2C_4F_9)^-$] having a purity of at least 99% was obtained. The yield was 91%.

EXAMPLE 9

In this example, the second salt (3) of the sulfonimide (1) was prepared by the steps (a) and (b) of the second method. The step (a) for obtaining the first salt (2) was conducted as follows.

At first, a flask was charged with 80 ml of acetonitrile, 33.7 g of perfluorooctylsulfonyl fluoride ($C_8F_{17}SO_2F$), 12.7 g of pyridine and 10.0 g of trifluoromethylsulfonyl amide ($CF_3SO_2NH_2$). Then, the reaction mixture was stirred at $50°$ C. for 3 hr. Then, the solvent was distilled out, to thereby obtain a first mixture of the first salt, i.e. pyridinium salt of perfluorooctylsulfonyltrifluoromethylsulfonyl imide [$C_5H_5NH^+(CF_3SO_2NSO_2C_8F_{17})^-$], and pyridinium fluoride [$C_5H_5NH^+F^-$].

In the step (b), the thus prepared first mixture was mixed with an aqueous solution containing 6.0 g of calcium hydroxide. After the reaction, the insoluble calcium fluoride was filtered out from the reaction mixture. Then, triethylamine and water as by-products were distilled out from the filtrate, to thereby obtain 39.6 g of the second salt, i.e. calcium salt of perfluorooctylsulfonyltrifluoromethylsulfonyl imide [$Ca(CF_3SO_2NSO_2C_8F_{17})_2$] having a purity of at least 99%. The yield was 91%.

EXAMPLE 10

In this example, the second salt (3) of the sulfonimide (1) was prepared by the steps (a) and (b) of the second method. The step (a) for obtaining the first salt (2) was conducted as follows.

At first, a flask was charged with 80 ml of acetonitrile, 33.5 g of pentafluorobenzenesulfonyl fluoride ($C_6F_5SO_2F$), 25.4 g of pyridine and 20.0 g of trifluoromethylsulfonyl amide ($CF_3SO_2NH_2$). Then, the reaction mixture was stirred at $50°$ C. for 3 hr. Then, the solvent was distilled out, to thereby obtain a first mixture of the first salt, i.e. pyridinium salt of pentafluorobenzenesulfonyltrifluoromethylsulfonyl imide [$C_5H_5NH^+(CF_3SO_2NSO_2C_6F_5)^-$], and pyridinium fluoride [$C_5H_5NH^+F^-$].

In the step (b), the thus prepared first mixture was subjected to the same treatment as that of the step (b) of Example 2 for obtaining the second salt, except in that the amount of sodium hydroxide was 10.8 g. With this, 48.4 g of the second salt, i.e. sodium salt of pentafluorobenzenesulfonyltrifluoromethylsulfonyl imide [$Na^+(CF_3SO_2NSO_2C_6F_5)^-$] having a purity of at least 99% was obtained. The yield was 90%.

What is claimed is:

1. A method of preparing a sulfonimide represented by the general formula (1), a first salt thereof represented by the general formula (2), or a second salt thereof represented by the general formula (3), the method comprising the step of:

(a) reacting one or two sulfonyl fluorides represented by the general formula (4) with nonhydrous ammonia and an amine component which is one of a tertiary amine represented by the general formula (5) and a heterocyclic amine, so as to prepare said first salt,

wherein "Rf¹" and "Rf²" represent the same or different groups each of which has a carbon atom number from 1 to 12 and is straight-chain or branched-chain and one selected from the group consisting of perfluoroalkyl groups, fluoroalkyl groups, fluoroalkenyl groups and fluoroallyl groups, $$M^1[Rf^1SO_2-N-SO_2Rf^2]_{n1} \qquad (2)$$

wherein "Rf¹" and "Rf²" are defined as above; "M¹" represents a positive ion having a first valence; and "n1" represents an integer that is the same as said first valence, $$M^2[Rf^1SO_2-N-SO_2Rf^2]_{n2} \qquad (3)$$

wherein "Rf¹" and "Rf²" are defined as above; "M²" represents an alkali or alkali earth metal atom having a second valence; and "n2" represents an integer that is the same as said second valence, $$RfSO_2F \qquad (4)$$

wherein "Rf" represents the same or different groups which are identical with said "Rf¹" and said "Rf²", $$(R_1)_3N \qquad (5)$$

wherein "R¹" represents the same or different alkyl groups each having a carbon atom number from 1 to 5.

2. A method according to claim 1, wherein, after the step (a), the method further comprises the step of:

(b) reacting, in an aqueous solution, said first salt with a metal compound selected from the group consisting of hydroxides, oxides and carbonates, said metal compound containing said alkali or alkali earth metal atom, so as to prepare said second salt.

3. A method according to claim 1, wherein, after the step (a), the method further comprises the step of:

(c) reacting the first salt with a strong acid so as to prepare said sulfonimide.

4. A method according to claim 2, wherein, after the step (b), the method further comprises the step of:

(d) reacting the second salt with a strong acid so as to prepare said sulfonimide.

5. A method of preparing a sulfonimide represented by the general formula (1), a first salt thereof represented by the general formula (2), or a second salt thereof represented by the general formula (3), the method comprising the step of:

(a) reacting a sulfonyl fluoride represented by the general formula (4) with an amine component which is one of a tertiary amine represented by the general formula (5) and a heterocyclic amine and a sulfonamide represented by the general formula (6), $$H[Rf^1SO_2-N-SO_2Rf^2] \qquad (1)$$

wherein "Rf¹" and "Rf²" represent the same or different groups each of which has a carbon atom number from 1 to 12 and is straight-chain or branched-chain and one selected from the group consisting of perfluoroalkyl groups, fluoroalkyl groups, fluoroalkenyl groups and fluoroallyl groups, $$M^1[Rf^1SO_2-N-SO_2Rf^2]_{n1} \qquad (2)$$

wherein "Rf¹" and "Rf²" are defined as above; "M¹" represents a positive ion having a first valence; and "n1" represents an integer that is the same as said first valence, $$M^2[Rf^1SO_2-N-SO_2Rf^2]_{n2} \qquad (3)$$

wherein "Rf¹" and "Rf²" are defined as above; "M²" represents an alkali or alkali earth metal atom having a second valence; and "n2" represents an integer that is the same as said second valence, $$RfSO_2F \qquad (4)$$

wherein "Rf" represents the same or different groups which are identical with said "Rf¹" and said "Rf²", $$(R^1)_3N \qquad (5)$$

wherein "R¹" represents the same or different alkyl groups each having a carbon atom number from 1 to 5, $$RfSO_2NH_2 \qquad (6)$$

wherein "Rf" is defined as above.

6. A method according to claim 5, wherein, after the step (a), the method further comprises the step of:

(b) reacting, in an aqueous solution, said first salt with a metal compound selected from the group consisting of hydroxides, oxides and carbonates, said metal compound containing said alkali or alkali earth metal atom, so as to prepare said second salt.

7. A method according to claim 5, wherein, after the step (a), the method further comprises the step of:

(c) reacting the first salt with a strong acid so as to prepare said sulfonimide.

8. A method according to claim 6, wherein, after the step (b), the method further comprises the step of:

(d) reacting the second salt with a strong acid so as to prepare said sulfonimide.

9. A method according to claim 1, wherein each of said "Rf¹" and said "Rf²" is a perfluoroalkyl group.

10. A method according to claim 5, wherein each of said "Rf¹" and said "Rf²" is a perfluoroalkyl group.

11. A method according to claim 9, wherein each said perfluoroalkyl group is a member selected from the group consisting of trifluoromethyl group, perfluorobutyl group, perfluorooctyl group, and pentafluorobenzene group.

12. A method according to claim 11, wherein each said perfluoroalkyl group is a member selected from the group consisting of said trifluoromethyl group and said perfluorobutyl group.

13. A method according to claim 10, wherein said perfluoroalkyl group is a member selected from the group consisting of trifluoromethyl group, perfluorobutyl group, perfluorooctyl group, and pentafluorobenzene group.

14. A method according to claim 13, wherein said perfluoroalkyl group is a member selected from the group consisting of said trifluoromethyl group and said perfluorobutyl group.

* * * * *